United States Patent [19]

Gaffar et al.

[11] 4,217,343

[45] Aug. 12, 1980

[54] MAGNESIUM POLYCARBOXYLATE COMPLEXES AS ANTICALCULUS AGENTS

[75] Inventors: Abdul Gaffar; Maria C. S. Gaffar, both of Somerset, N.J.

[73] Assignee: Colgate Palmolive Company, New York, N.Y.

[21] Appl. No.: 42,485

[22] Filed: May 25, 1979

Related U.S. Application Data

[62] Division of Ser. No. 861,795, Dec. 12, 1977, Pat. No. 4,183,914.

[51] Int. Cl.$^2$ .......................... A61K 9/68; A61K 7/16
[52] U.S. Cl. ....................................... 424/48; 424/49
[58] Field of Search .................................. 424/48–58

[56] References Cited

U.S. PATENT DOCUMENTS

| | | | |
|---|---|---|---|
| 1,817,664 | 8/1931 | Badanes | 424/49 |
| 3,429,963 | 2/1969 | Shedkovsky | 424/56 |
| 3,452,049 | 6/1969 | Globus | 260/343 P |
| 3,558,769 | 1/1971 | Globus | 424/54 |
| 3,689,636 | 9/1972 | Svajda | 424/49 |
| 3,956,480 | 5/1976 | Dichter et al. | 424/54 |
| 3,991,177 | 11/1976 | Vidra et al. | 424/50 |
| 4,058,595 | 11/1977 | Colodney | 424/50 |
| 4,152,420 | 5/1979 | Gaffar et al. | 424/56 |
| 4,183,914 | 1/1980 | Gaffar et al. | 424/49 |

FOREIGN PATENT DOCUMENTS 2164383  8/1972  Fed. Rep. of Germany.

OTHER PUBLICATIONS

Van Barthold, Gor. Off., 2,164,383, Aug. 17, 1972, per Chem. Abstr. 77:168507s, (1972).
Begala et al., J. Phys. Chem., 76(2): 254–260, (1972) per Chem. Abstr. 76:154337w, (1972).
Purdig et al., Phys. Chem. 75(8): 1136–1140, (1971), per Chem. Abstr. 75:21225R, (1971).
Crisp et al., J. Dent. Res. 55(2): 299–308, May–Apr. 1976.

Primary Examiner—Shep K. Rose
Attorney, Agent, or Firm—Robert L. Stone; Murray M. Grill; Herbert S. Sylvester

[57] ABSTRACT

A novel composition to prevent and control dental calculus containing as the essential agent, a magnesium polycarboxylate complex formed by the reaction or interaction of a magnesium compound with a polycarboxylate selected from the group consisting of maleic acid copolymers, sulfoacrylic acid oligomers, and tricarboxy-oxa-butanol or pentanol.

7 Claims, No Drawings

MAGNESIUM POLYCARBOXYLATE COMPLEXES AS ANTICALCULUS AGENTS

This is a division of application Ser. No. 861,795 filed Dec. 12, 1977, now U.S. Pat. No. 4,183,914, issued Jan. 15, 1980.

This invention relates to novel oral formulations comprising a combination of a magnesium compound with maleic acid copolymer or a sulfoacrylic acid oligomer, or a tricarboxy-oxa-butanol or pentanol as an effective agent against calculus formation.

DESCRIPTION OF THE PRIOR ART

The prior art is replete with oral compositions containing magnesium salts such as magnesium oxide, hydroxide, carbonate, silicate or phosphate to prevent decalcification of tooth enamel as disclosed in U.S. Pat. No. 2,216,821 by Lang; magnesium chloride as a desensitizer of sensitive teeth in U.S. Pat. No. 3,689,636 to Svajda; and magnesium amino-alkylene phosphonate as a dental polishing agent in U.S. Pat. No. 3,642,979.

The prior art also discloses many anticalculus agents, most of which are particular phosphonic acid compounds and their pharmaceutically acceptable salts which include the alkaline earth metals such as magnesium. The anticalculus activity is attributed to the phosphonic acid compounds per se as shown by U.S. Pat. Nos. 3,488,419 and 3,678,154, wherein are disclosed polyphosphonates containing two to nine phosphonic radicals; the Francis patents, U.S. Pat. Nos. 3,553,314, 3,553,315, 3,584,116, 3,683,080 and 3,737,522 also disclosing the polyphosphonates; a tri-phosphonated amine disclosed in U.S. Pat. No. 3,639,569; and pyrolidine-diphosphonates disclosed in U.S. Pat. No. 3,960,888. These phosphonates have replaced the calcium chelsting agents heretofore, used as a means of preventing, retarding, and removing calculus formation, since chelating agents tend to damage the tooth enamel. Examples of sequestering agents capable of removing soft tartar and other calcium deposits from teeth without any adverse side effects is disclosed in the Globus U.S. Pat. Nos. 3,452,049 and 3,558,769, namely the magnesium polyalkanolamino ethylene diamine tetraacetate:glucono citrate complex. Although the polyphosphonates represent an improvement over the chelating agents as effective anticalculus agents, said phosphonates have been found to adversely affect the post eruptive maturation of dental enamel as shown in the Widder U.S. Pat. No. 3,678,154, wherein is disclosed the addition of a water soluble fluoride compound to counteract said adverse effect.

The use of a cyclohexane-hexacarboxylic acid and water soluble salts thereof including the magnesium salt in the therapeutic treatment of tartar is disclosed in U.S. Pat. No. 3,920,837.

An ammonium polyacrylic acid salt or an ammonium-polyacrylic acid polymer complex have also been used in dentifrice formulations for its demineralization-inhibiting and mineralization-promoting effects on dental enamel, as disclosed in German Pat. No. 2,164,383.

Also known is the use of a water soluble sodium salt of a linear anionic polymer as an anti-calculus agent, as set forth in U.S. Pat. No. 3,429,963 to Shedlovsky. This patent discloses that the hydrolyzed copolymers and/or polymers prevent the deposition of calculus by means of their calcium sequestration properties. U.S. Pat. No. 3,956,480 further discloses a combination of a cationic germicide and an anionic polymer as an effective inhibitor of calculus formation. U.S. Pat. No. 3,934,002 discloses a wide assortment of anti-calculus agents defined in prior art patents together with a bis-biguanide in a non-staining oral composition. However, there is no suggestion in these patents, nor in any of the known prior art, that the combination of a magnesium salt with the specific group of the aforedefined polycarboxylates is unusually effective in preventing and controlling calculus, over a protracted period of time, without adversely affecting the tooth enamel.

Accordingly, it is an object of this invention to provide an oral composition containing as the anti-calculus agent, the reaction product of a magnesium salt with a polycarboxylate selected from the group consisting of the maleic acid copolymers, the oligomer of sulfoacrylic acid and the tricarboxy-oxa-butanol or pentanol, and the alkali metal salts thereof.

Another object of instant invention is to provide an oral composition effective in inhibiting calculus formation over a protracted period of time.

Still another object of this invention is to provide an oral composition effective in inhibiting plaque, calculus, caries and periodontal disease.

BACKGROUND OF THE INVENTION

It is well known in the art that the mineralization of dental deposits and the subsequent formation of calculus (hydroxyapatite deposit) occurs via a homogenous nucleation (an increase in $Ca^{++}$ ions or orthophosphate ions) and/or via heterogeneous nucleation (specific salivary and bacterial proteins). However, in either case, salivary $Ca^{+2}$ is added to the salivary orthophosphate leading to hydroxyapatite (HAP) formation. The formation of HAP in vitro occurs in two distinct steps:

1. When $Ca^{+2}$ is added to orthophosphate at constant pH (7.4, by pH stat), there is rapid consumption of base as a function of time, that is, 1–4 minutes.
2. Then the base consumption diminishes for about 15–20 minutes after which the second uptake of base occurs. A delay in the time of the second rapid consumption of base, or a total absence of a second rapid consumption suggests an interference with the crystal growth of HAP. Accordingly, compounds which interfere with crystal growth of HAP are effective anti-calculus agents.

It is also known that the magnesium ion, $Mg^{+2}$, reduces the overall rate of crystallization by stabilizing the precursor (amorphous deposit) formed initially with $Ca^{+2}$ and orthophosphate, as disclosed in "Growth of Calcium Phosphates on Hydroxyapatite Crystals: The Effect of Magnesium". Arch. Oral Biol, 20:803, 1975. The amorphous deposits are readily removable while the crystalline phase is difficult to remove. However, the residence time of externally introduced $Mg^{+2}$ ion in the oral cavity is low. Saliva also has an extremely low $Mg^{+2}$ content (J. Periodontal Res. 9:211–221, 1974).

It has now been found that the efficacy of the magnesium ions can be improved by combining magnesium with a polycarboxylate selected from the group consisting of the maleic acid copolymers, the sulfoacrylic oligomers and the tricarboxy-oxa-butanol or pentanol to form a complex therewith. Since there are at least two carboxyl groups per mole of polycarboxyl-containing compound (e.g. two carboxyl groups per mole of maleic acid), one carboxyl is available to react with $Mg^{+2}$ (⅔ ionized) and there are enough free $COO^-$ to react with the tooth enamel.

DESCRIPTION OF THE INVENTION

It has also been found, that the particular group of polycarboxy compounds used herein are substantive to tooth enamel. Accordingly, an effective method of inhibiting calculus formation entails the use of an oral composition comprising a magnesium polycarboxylate complex formed by combining magnesium compounds with said polycarboxyl containing compounds. The positively charged magnesium ions can react with the free carboxyl groups of the polycarboxylate to form magnesium polycarboxylate complexes. In the mouth, the magnesium combinations or complex adsorbs onto the oral surfaces such as the teeth and oral mucosa, thereby forming a reservoir of magnesium ions capable of being gradually released with time into the oral environment. Thus, the magnesium polycarboxylate complex of instant invention, will have greater substantivity to the tooth enamel than the magnesium ion per se, and provide $Mg^{+2}$ ions from this complex for a longer period of time.

Accordingly, it has now been found that calculus formation can be inhibited without adversely affecting the tooth enamel by treating the oral cavity with a combination of a magnesium compound and a polycarboxylate. Said magnesium polycarboxylate complex provides both a means of attachment to the oral cavity as well as a reservoir of magnesium ions which are gradually released over a protracted period of time as an effective means to combat plaque, and calculus.

More specifically, this invention relates to an oral composition containing as the essential anticalculus agent, a magnesium polycarboxylate complex wherein said polycarboxylate contains ionizable carboxyl groups selected from the group consisting of:

1. a copolymer of maleic acid or anhydride and of an olefin having 2 or more carbon atoms per molecule,
2. sulfoacrylic oligomers having an average molecular weight of less than 1000, and
3. a tricarboxy-oxa-butanol or pentanol, and is ionically bound to a dissociable, physiologically acceptable magnesium compound.

The polycarboxyl-containing compounds which form a complex with the magnesium are well known in the art. They contain ionizable carboxyl groups and are selected from the group consisting of the copolymers of maleic acid or anhydride and of an olefin having 2 or more carbon atoms per molecule, the sulfoacrylic oligomers and tricarboxy-oxa-butanol or pentanol. They are preferably water soluble per se or the alkali metal or ammonium salts thereof are water soluble, at least to the extent of the concentration in which employed, about 0.1 to 10%, and preferably 0.5–1.5% of the oral composition. Suitable examples include the copolymers of maleic anhydride or acid with ethylene, styrene, isobutylene, methyl vinyl ether or ethyl vinyl ether having recurring groups:

wherein M and $M_1$ are individually hydrogen, sodium, potassium or ammonium and may be the same or different, and X is ethylene, styrene, isobutylene, methyl vinyl ether or ethyl vinyl ether.

Oligomers generally and their preparation are described in U.S. Pat. No. 3,859,260. The sulfoacrylic oligomers used herein have an average molecular weight of less than 1000 and can be represented by the following structure:

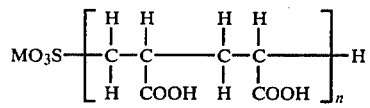

wherein M is an alkali metal or the ammonium ion, and n is less than 10 and greater than 6. The sulfonate group is not proximate to the carboxylate group. This group of sulfoacrylic oligomers have been found to be active per se in inhibiting hydroxyapatite formation in concentrations of $3 \times 10^{-4}$ M or 33 ppm as evidenced by the following results:

TABLE I

| Inhibitor | Concentration | t (delay in HAP formation) | $Ca^{++}$:Inhibitor |
|---|---|---|---|
| Sulfoacrylic oligomer[1] (ND-2 of mol. < wt. 1000) | $3 \times 10^{-4}$ M | 17 minutes | 10:1 |
| $MgCl_2$:ND-2(1:3) | $1 \times 10^{-4}$ M | 23 minutes | 40:1 n < 10 |

$$1 \quad MO_3S\!-\!\!\left[\begin{array}{cccccccc} H & H & H & H & H & H & H & H \\ | & | & | & | & | & | & | & | \\ C\!-\!C & \!-\!\!C\!-\!C & \!-\!\!C\!-\!C & & C\!-\!C \\ | & | & | & | & | & | & | & | \\ H & COOH & & COOH & & COOH & H & COOH \end{array}\right]_n\!\!-\!H$$

It is additionally evident by the greater t value that the magnesium complex of the sulfoacrylic oligomer is more effective than the oligomer per se in inhibiting HAP crystal growth even in more dilute concentrations.

On the contrary, other polymeric polycarboxylates such as the dimer of acrylic acid, polyacrylic acid polymers of molecular weights of 2000 or higher, and higher molecular weight polycarboxylate polymers including the polymaleates have been found to be inactive even at greater concentrations (i.e. $8.0 \times 10^{-4}$ M). In addition, the polyacrylic acid polymers exhibit no substantivity to tooth enamel.

The low molecular weight polymaleates represented by the following structure:

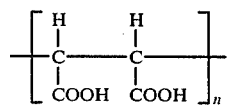

wherein n is less than 5 have also been found to be active per se as evidenced by the following table wherein the delay in time of the crystal growth of HAP was measured in the presence of these polymaleates.

TABLE II

| n | Concentration | t (delay time) |
|---|---|---|
| 5.0 | $4 \times 10^{-4}$ M | not active |
| 4.0 | $4 \times 10^{-4}$ M | 40 minutes |
| 3.0 | $1 \times 10^{-4}$ M | 30 minutes |

However, it has been found that the magnesium complex of the higher molecular weight polymaleate polymers are active in inhibiting crystal growth of HAP as evidenced by the results tabulated below:

TABLE III

| Inhibitor | Concentration | t (minutes) | $Ca^{++}$:Inhibitor |
|---|---|---|---|
| Maleic - Vinyl methyl ether copolymer (mol. wt. 250,000) pH 7.4 | $1 \times 10^{-4}$ M<br>$3 \times 10^{-4}$ M | none<br>none | 10:1 |
| $MgCl_2$ | $1 \times 10^{-4}$ M<br>$1.2 \times 10^{-4}$ M | 5<br>18 | 40:1<br>13.3:1 |
| pH 7.4 | $3 \times 10^{-4}$ M | 53 | 10:1 |
| Mg complex of maleic-vinyl methyl ether copolymer (mol. wt. 250,000) (1:1 mole ratio) | $1 \times 10^{-4}$ M | 29 | 40:1 |
| Mg complex of maleic-vinyl methyl ether copolymer (mol. wt. 250,000) (1:2 mole ratio) | $1 \times 10^{-4}$ M | 26 | 40:1 |
| Mg complex of maleic-vinyl methyl ether copolymer (mol. wt. 250,000) (2:1 mole ratio) | $1 \times 10^{-4}$ M | 26 | 40:1 |
| $MgCl_2$ + maleic-vinyl methyl ether copolymer (mol. wt. 250,000) (1:4 mole ratio) | $1 \times 10^{-4}$ M | 88 | 40:1 |

These results additionally show that these magnesium polycarboxylate (maleic copolymer) complexes are more effective in inhibiting crystal growth of HAP than the magnesium ion alone.

The tricarboxy-oxa-butanol and pentanol per se have been found to be inactive in inhibiting crystal growth of HAP, whereas the magnesium complex thereof are effective as inhibitors of HAP crystal growth as shown by the following results:

TABLE IV

| Inhibitor | Concentration | t (minutes) | $Ca^{++}$:Inhibitor |
|---|---|---|---|
| OTB[1] | $4 \times 10^{-4}$ M | none | 10:1 |
| $MgCl_2$:OTB (1:1) | $1 \times 10^{-4}$ M | 16 | 40:1 |
| $MgCl_2$:OTB (1:1) | $2 \times 10^{-4}$ M | 26 | 20:1 |
| $MgCl_2$:OTB (1:1) | $3 \times 10^{-4}$ M | 68 | 13.3:1 |

[1] OTB is 3-oxa-2,2,4 tricarboxybutanol-1, trisodium salt represented by the following structural formula:

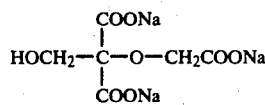

Although citric acid is a tricarboxy acid, it has been found to be ineffective to inhibit the growth of HAP crystals. It exhibits no substantivity to tooth enamel and poor diffusion in aqueous medium. The unusual and unexpected effectiveness of the above tricarboxy compounds may be due to the presence of the hydroxyl group and/or the particular configuration of said compounds.

The magnesium compounds that form the magnesium polycarboxylate complex by reaction or interaction with said polycarboxylate may be any dissociable, physiologically acceptable magnesium salt including the water soluble and insoluble, organic and inorganic magnesium salts. Examples of suitable magnesium compounds that may be employed include:

| | |
|---|---|
| magnesium acetate | magnesium isovalerate |
| magnesium acetylacetonate | magnesium D-lactate |
| magnesium ammonium sulfate | magnesium DL-lactate |
| magnesium benzoate | magnesium laurate |
| magnesium bromide | magnesium hexafluorosilicate |
| magnesium beryllium orthosilicate | magnesium methacrylate |
| magnesium borate | magnesium molybdate |
| magnesium butylphthalate | magnesium naphthenate |
| magnesium butylxanthate | magnesium octoate |
| magnesium caprylate | magnesium oleate |
| magnesium carbonate | magnesium orthophosphate |
| magnesium chloroanilate | magnesium phenolsulfonate |
| magnesium chlorate | magnesium pyridine-2-thiol-1-oxide |
| magnesium chromate | |
| magnesium citrate | magnesium pyrophosphate |
| magnesium cyclohexane butyrate | magnesium resinate |
| magnesium chloride | magnesium salicylate |
| magnesium gallate | magnesium sulfate |
| magnesium fluoride | magnesium nitrate |
| magnesium alpha-glucoheptonate | magnesium selenide |
| magnesium gluconate | magnesium stearate |
| magnesium glycerophosphate | magnesium sulfanilate |
| magnesium hydroxide | magnesium tartrate |
| magnesium 8-hydroxyquinoline | magnesium tellurate |
| magnesium 12-hydroxystearate | magnesium tungstate |
| magnesium iodide | magnesium valerate |
| magnesium acrylate | magnesium vanadate |
| magnesium oxide | magnesium tribromosalicylanilide |
| magnesium propionate | magnesium ricinoleate |

The majority of the magnesium salts are water-soluble. Many insoluble magnesium salts are rendered soluble when combined with the polycarboxylate, thereby providing a means of following the interaction or reaction between magnesium and the polycarboxylate. The magnesium compound constitutes about 0.01-5% and preferably 0.025-1% by weight of the oral composition.

Aqueous dispersions or solutions of magnesium polycarboxylate complexes may be produced by adding a magnesium salt in the form of a dilute solution, a paste or in the dry state, to a dilute solution of polycarboxylate, and stopping the addition before the amount of magnesium salt is such as to form a precipitate or gel. With good agitation and careful addition not to exceed the amount of maximum solubility of the magnesium polycarboxylate complex, a clear solution or dispersion is obtained. This phenomena is clearly indicated in Example 2. The polycarboxylate solution is preferably adjusted to a pH of about 7.0 with ammonium hydroxide or other suitable base prior to the addition of the magnesium salt. The pH of the final magnesium polycarboxylate solution is about 4.5-7.8. For example, a suitable magnesium polycarboxylate complex is formed by adding 0.4% of a magnesium salt solution such as $MgCl_2$ to 100 ml of a 0.1% solution of a copolymer of methylvinyl ether and maleic anhydride, (adjusted to a pH of 7.0 with ammonium hydroxide) and mixing well. The final solution or dispersion of the magnesium maleic copolymer complex preferably has a pH of about 4.5-7.8. It is believed that the ionized carboxyl groups react or interact with the magnesium ion to form a magnesium copolymer complex. See the article by Crisp et al, J. Dent. Res. March-April 1976, 55, 2, pp. 299–308, particularly pp. 305–307; and by Begala et al, The Journal of Physical Chemistry (1972), 76, 2, pp. 254–260 dealing with counterion binding by polycarboxylates. The experimental evidence shows that the binding of magnesium to polymers is mostly ionic. Ionic binding leads to either:

(a) chain bridging salts:

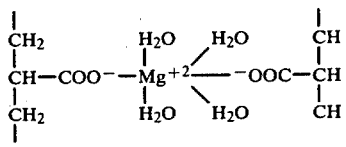

(b) intra chain salts:

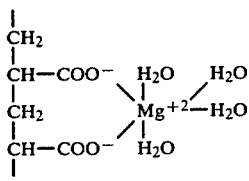

(c) pendant half salts:

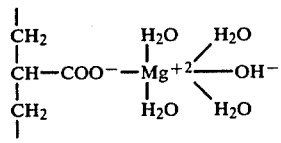

(d) chelate (ring) structures with copolymers of vinylmethyl ether and maleic anhydride, since divalent cations like magnesium form a chelate with the ether oxygen and one carboxyl group:

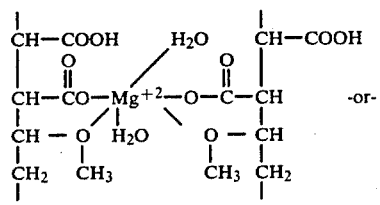

-or-

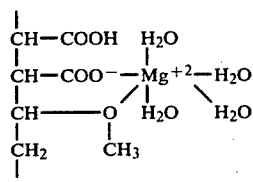

Accordingly, it is believed that the magnesium carboxylate complex is ionically bound, but the exact type of binding (which may also exist as a mixture of above structures) has not been ascertained.

The following examples are given to illustrate this invention further. In this application all proportions are by weight unless otherwise indicated.

EXAMPLE 1

0.2 gm magnesium chloride is dissolved in 15 ml water and added to a 4% aqueous solution of the copolymer of maleic anhydride and methylvinyl ether with agitation and subsequently diluted to 200 ml. A clear solution of the magnesium copolymer complex is obtained.

EXAMPLE 2

(a) 100 g of an aqueous magnesium oxide paste containing 0.5% magnesium is prepared and added slowly with continuous stirring to 25 ml of a 1% aqueous solution of methylvinyl ether-maleic anhydride copolymer and subsequently diluted with 75 ml water. The final solution has a pH of 5.5 and is slightly cloudy. The ratio of magnesium to copolymer is 1:2.

(b) 100 gm of an aqueous magnesium oxide paste containing 0.25% magnesium is added to 100 gm of an aqueous solution containing 0.25% methylvinyl ether-maleic anhydride copolymer with continuous agitation. The final solution has a pH of 6.5 and is turbid. The ratio of magnesium to anionic polymer is 2:1.

(c) A final solution of magnesium copolymer complex is prepared as above containing 0.25% magnesium and 1.0% maleic copolymer, a ratio of 1:4, which has a pH of 3.5 and is clear. With the addition of about 10 ml. 3 N ammonium hydroxide to said clear solution, the pH is adjusted to 6.8 (pH in the oral cavity) and the solution retains its clarity.

This example clearly shows that the ratio of magnesium salt to maleic copolymer is dependent on the solubility of the final magnesium copolymer complex formed, maximum solubility being evidenced by a clear solution which is preferable although a slight cloudiness is also acceptable.

EXAMPLE 3

A magnesium copolymer complex is prepared by mixing 50 ml of 0.05 M aqueous solutions of the following magnesium salts with 50 ml of a 2% aqueous solution of methylvinyl ether-maleic anhydride copolymer and the pH is adjusted to 5–6 with ammonium hydroxide. The ratio of magnesium to maleic copolymer is 1:4.
a. magnesium oxide which is water insoluble.
b. magnesium chloride which is water soluble.
c. magnesium glycerophosphate which is soluble in water.
d. magnesium salicylate which is soluble in water.
e. magnesium alpha glucoheptonate which is water soluble.
f. magnesium propionate which is soluble in water.
g. magnesium salt of 8-hydroxyquinoline which is water insoluble.
h. magnesium gluconate which is water soluble.
i. magnesium pyrophosphate which is insoluble in water, but soluble in dilute mineral acids.

The final solutions or dispersions containing the magnesium maleic copolymer complex were all clear. Although the ratio of magnesium salt to polycarboxylate in this example is 1:4, this ratio may be varied over a wide range, e.g. 1:40 to about 4:1.

While particularly good results in terms of calculus inhibition and other salutary effects in the oral cavity and on tooth surfaces, have thus far been obtained by applying simply the aqueous solutions or dispersions of the magnesium polycarboxylate complex, it will be understood that it is within the broader aspect of the invention to incorporate said complex into oral compositions generally, such as clear or cloudy mouth rinses and transparent or opaque toothpastes, troches, chewing gum, tablet or powder containing a dental vehicle. Likewise, the complex may be formed in situ, during the preparation of said oral compositions or even on dilution in the mouth; or the magnesium compound and the polycarboxylate may merely act cooperatively within said oral cavity and not form a detectable complex.

The vehicle, often referred to as a dental vehicle contains liquids and solids. In general, the liquid comprises water and/or a humectant such as glycerine, sorbitol, propylene glycol or polyethylene glycol 400 including suitable mixtures thereof. It is usually advantageous to use a mixture of both water and one or two humectants. The total liquid content is generally about 20-90 percent by weight of the vehicle. In transparent and translucent vehicles, the liquid content of the toothpaste may be about 20-90 percent by weight, while in opaque vehicles the total liquid content is usually about 20-50 percent by weight. The preferred humectants are glycerine and sorbitol. Typically clear, that is transparent or translucent, vehicle contains 0-80 percent by weight of glycerine, about 20-80 percent by weight of sorbitol and about 20-80 percent by weight of water. Opaque vehicles typically contain about 15-35 percent by weight of glycerine and about 10-30 percent by weight of water.

The solid portion of the vehicle is a gelling agent. In the instant invention the gelling agent includes alkali metal carboxymethyl cellulose in amounts of at least about 0.25 percent by weight of the vehicles. Additional gelling agents may also be present. Gelling agents which may be additionally present include viscarin, gelatin, starch, glucose, sucrose, polyvinyl pyrrolidone, polyvinyl alcohol, gum tragacanth, gum karaya, hydroxy propyl cellulose, methyl cellulose carboxyethyl cellulose, sodium alginate, Laponite CP or SP, which are each synthetic inorganic complex silicate clays solid under trademark by Laporte Industries, Ltd., and magnesium aluminum silicate gel. The solid portion or gelling agent of the vehicle is typically present in amounts of about 0.25-10 percent by weight of the toothpaste and preferably about 0.5-8 percent by weight. Alkali metal carboxymethyl cellulose includes the lithium, sodium and potassium salts.

Any suitable substantially water-insoluble polishing agent may be added to the gel vehicle. There is a relatively large number of such materials known in the art. Representative materials include, for example, dicalcium phosphate, tricalcium phosphate, insoluble sodium metaphosphate, aluminum hydroxide, calcined alumina, magnesium carbonate, calcium carbonate, calcium pyrophosphate, calcium sulfate, bentonite, etc., including suitable mixtures thereof. It is preferred to use the water-insoluble phosphate, sodium metaphosphate and/or a calcium phosphate, such as dicalcium diphosphate dihydrate. The present magnesium polycarboxylate complexes have been found to stabilize the monofluorophosphates in an oral composition containing the diphosphate dihydrate abrasive. In general, these polishing agents will comprise a major proportion by weight of the solid ingredients. The polishing agent content is variable, but will generally be up to about 75 percent by weight of the total composition, generally about 20-75 percent; although, as indicated below, even lower amounts of polishing agent can be employed.

Any suitable surface-active or detersive material may be incorporated in the gel vehicle. Such compatible materials are desirable to provide additional detersive, foaming and antibacterial properties depending upon the specific type of surface-active material and are selected similarly. These detergents are water-soluble organic compounds usually, and may be anionic, non-ionic, or cationic in structure. It is preferred to use the water-soluble non-soap or synthetic organic detergents, usually. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropanesulfonate) and the like.

The various surface-active materials may be used in any suitable amount, generally from about 0.05 to about 10 percent by weight, and preferably from about 0.5 to 5 percent by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical, and is more particularly described in U.S. Pat. No. 2,689,170 issued Sept. 14, 1954. The amino acid portion is derived generally from the lower aliphatic saturated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine, and sodium N-lauroyl glycine and alanine. For convenience herein, reference to "amino carboxylic acid compound", "sarcoside", and the like refers to such compounds having a free carboxylic group or the water-soluble carboxylate salts.

Various other materials may be incorporated in the vehicles of this invention. Examples thereof are preservatives, silicons, chlorophyll compounds, ammoniated materials such as urea, diammonium phosphate and mixtures thereof, materials which can increase contrast with the particles, such as zinc oxide or titanium dioxide and other constituents. These adjuvants are incorporated in the instant compositions in amounts which do not substantially adversely affect the properties and characteristics suitably selected and used in proper amount depending upon the particular type of preparation involved.

Antibacterial agents may also be employed in the gelled vehicles of the instant invention. Typical antibacterial agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
$N^1$-3-lauroxypropyl-$N^5$-p-chlorobenzylbiguanide;
1,6-di-p-chlorophenylbiguanide hexane;
1-(lauryldimethylammonium)-8-(p-chlorobenzyldimethylammonium) octane dichloride;
5,5-dichloro-2-guanidinobenzimidazole;
$N^1$-p-chlorophenyl-$N^5$-laurylbiguanide;
5-amino-1,3-bis(2-ethylhexyl)-3-methylhexahydro pyrimidine;
and their non-toxic acid addition salts.

The antibacterial agent, when present, is employed in amounts of about 0.1–5 percent by weight, preferably about 0.05–5 percent.

Any suitable flavoring or sweetening materials may be employed in formulating a flavor for the compositions of the present invention. Examples of suitable flavoring constituents include the flavoring oils, etc., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5 percent or more of the compositions of the instant invention.

A fluorine-containing compound having a beneficial effect on the care and hygiene of the oral cavity, e.g., diminution of enamel solubility in acid and protection of the teeth against decay may also be incorporated in the gelled vehicle. Examples thereof include sodium fluoride, stannous fluoride, potassium fluoride, potassium stannous fluoride ($SnF_2$—KF), sodium hexafluorostannate, stannous chlorofluoride, sodium fluorozirconate, and sodium monofluorophosphate. These materials, which disassociate or release fluorine-containing ions in water, suitably may be present in an effective but non-toxic amount, usually within the range of about 0.01 to 1 percent by weight of the water-soluble fluorine content thereof.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30 to 90 seconds at least once daily. Typical oral preparations of the invention which can be applied in this manner are set forth below.

EXAMPLE 4

Preparation of Magnesium Polycarboxylate Mouthrinse

Total volume = 1 liter

| Solution A (Mouthrinse concentrate) | % (gms/100 ml) | On Mixing with B Final conc: % |
|---|---|---|
| Ethyl alcohol | 20 | 10 |
| Pluronic F-108* | 8 | 4 |
| Flavor | 0.4 | 0.2 |
| Glycerin | 20 | 10 |
| Saccharin | 0.06 | 0.03 |
| 0.1% FD & C Color | 0.6 | 0.3 |

| Solution A (Mouthrinse concentrate) | % (gms/100 ml) | On Mixing with B Final conc: % |
|---|---|---|
| Deionized water q.s. | to 100.00 | |

*A polyalkene oxide block polymer

Solution B

Magnesium Polycarboxylate Complex

A 2% copolymer solution is prepared by adding methylvinyl ethyl-maleic anhydride copolymer (Gantrez) to 500 ml of water. The pH is adjusted to 5.5 by the addition of 3 N ammonium hydroxide. Then 0.050 M of magnesium oxide salt is added with stirring. The mixture is a clear solution.

500 ml of solution A is added to 500 ml of solution B with continuous stirring (e.g. magnetic stirrer). The pH of the mixture is between 4 and 6, and is a clear mouth rinse. The final concentration of magnesium salt in the mouthrinse is 0.025 M and of the copolymer is 1%.

Equilibrium dialysis studies showed that the magnesium maleic copolymer complex in a typical mouth rinse formulation retains its identity in the presence of saliva salts and exhibits a slow rate of dissociation. The slow release of the magnesium ions and the increased retention of the magnesium in the oral cavity enhance the effectiveness of instant oral compositions containing the magnesium copolymer complex against dental calculus formation and other oral disorders.

EXAMPLE 5

| Mouthwash | % |
|---|---|
| Ethyl alcohol | 5.0 |
| Non-ionic detergent (Pluronic F-108)[1] | 3.0 |
| Flavor | 0.073 |
| Glycerin | 10.0 |
| Saccharin | 0.03 |
| Gantrez 119 (20 ml of 0.5% aqueous solution)[2] | 0.1 |
| Magnesium chloride | 0.4 |
| Water q.s. | to 100 |

[1] A polyalkene oxide block polymer
[2] Copolymer of maleic anhydride and methylvinyl ether having a molecular weight of 250,000.

The magnesium chloride powder is added to a 0.5% aqueous solution of the copolymer and stirred until dissolved and the pH is adjusted to 7.00 with ammonium hydroxide and then the mouth rinse concentrate containing the remaining ingredients is added to the magnesium copolymer solution. A clear mouthwash having a pH of 5.3 is produced which is very effective in inhibiting dental calculus formation over a protracted period of time. The ratio of magnesium salt to polycarboxylate is 4:1.

EXAMPLE 6

A mouth wash is prepared in accordance with the procedure of Example 5, except that 1.0% of the sulfoacrylic oligomer ND-2 defined in Table I is substituted for the 0.1% of the maleic copolymer. A clear mouthrinse having a pH of 7.8 is produced which is an effective anti-calculus composition for a protracted period of time. The ratio of magnesium salt to oligomer is 2:5.

EXAMPLE 7

A mouthrinse in accordance with Example 5 is prepared except that 0.5% of the tricarboxylate OTB defined in Table IV, is substituted for the 0.1% of the maleic copolymer. The resultant mouthrinse is clear and has a pH of 7.0, and a magnesium:polycarboxylate ratio of 4:5.

EXAMPLE 8

| Dental Cream | |
|---|---|
| | % |
| Copolymer of Example 1 | 1.0 |
| Magnesium chloride | 0.025 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water q.s. | to 100.00 |

*Tween 80-Polyoxyethylene (20 moles ethylene oxide) sorbitan monooleate.

The magnesium copolymer complex is prepared in accordance with the procedure of Example 4. The remaining ingredients are admixed with agitation to form a base paste, which is then mixed with the magnesium copolymer complex, using either equal volumes or weights of the base paste and the preformed magnesium copolymer complex.

An effective amount, e.g., about 0.01-5% magnesium compound and 0.1 to 10% polycarboxylate may also be incorporated in an inert carrier or dissolved in a suitable vehicle in the formulation of chewing gums and lozenges. Similarly, the magnesium polycarboxylate complex may also be incorporated into a mouth spray. A typical lozenge formula contains the following ingredients, in percent by weight, based on the weight of the total formulation:

75% to 98%: Sugar
1% to 20%: Corn Syrup
0.1% to 1%: Flavor oil
0% to 0.03%: Colorant(s)
0.1% to 5%: Tableting Lubricant
0.2% to 2%: Water
0.1% to 10%: Polycarboxylate
0.01% to 5%: Magnesium compound.

Sugarless pressed candy may also be formulated to include the complex of this invention. For products of this type, which usually contain powdered sorbitol instead of sugar, synthetic sweeteners are mixed with the powdered sorbitol and flavor(s), colorant(s) and a tablet lubricant are then added. The formula is introduced into a tablet machine to shape the final product. A typical sugarless pressed candy contains the following ingredients, in percent by weight, based on the weight of the total formulation:

98% to 99.5%: Sorbitol
0.1% to 0.9%: Flavor(s)
0% to 0.02%: Synthetic Sweeteners
0% to 0.03%: Colorant(s)
0.05% to 1.00%: Tableting Lubricant.

Obviously many variations of the above described procedures may be used to prepare pressed candies.

A typical chewing gum may contain the following ingredients, in percent by weight based on the weight of the total gum formulation:

| Ingredients | Weight Percent |
|---|---|
| Gum Base | From about 10% to about 40% |
| Sucrose | From about 50% to about 75% |
| Corn Syrup or Glucose | From about 10% to about 20% |
| Flavor Material | From about 0.4% to about 5% |
| Polycarboxylate | From about 0.1% to about 10% |
| Magnesium Compound | From about 0.01% to about 5% |

An alternate chewing gum formulation is as follows:

| Ingredients | Weight Percent |
|---|---|
| Gum Base | From about 10% to about 50% |
| Binder | From about 3% to about 10% |
| Filler (Sorbitol, Mannitol or combinations thereof) | From about 5% to about 80% |
| Artificial Sweetener and Flavor | From about 0.1% to about 5% |
| Polycarboxylate | From about 0.1% to about 10% |
| Magnesium Compound | From about 0.01% to about 5% |

In certain sugarless gums, there is used as the binder ingredient a solution of sorbitol in water containing from about 10% to about 80%, preferably from about 50% to about 75% by weight of sorbitol in $H_2O$. In others, there is used a gum acacia-in-water system containing from about 30% to about 60%, preferably from about 45% to about 50% by weight of gum acacia powder.

The above chewing gum formulations are exemplary only. Many additional formulations are described in the prior art, and in carrying out this invention, such formulations can be employed. It is also possible to prepare an acceptable chewing gum product containing a gum base, flavoring material and magnesium polycarboxylate complex according to the teaching of this invention.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutyleneisoprene copolymer, paraffin, petroleum wax, polyethylene, polyisobutylene, polyvinylacetate, etc.; plasticizers such as lanolin, stearic acid, sodium stearate, potassium stearate, etc.

A preferred ingredient of instant composition is a non-ionic organic surfactant which provides increased prophylactic action, assists in achieving thorough and complete dispersion of instant compositions throughout the oral cavity and renders instant compositions more cosmetically acceptable. The non-ionic surfactant imparts to the composition detersive and foaming properties, as well as maintains the flavoring materials in solution (i.e., solubilizes flavor oils). In addition, the non-ionics are completely compatible with the magnesium polycarboxylate complex of this invention, thereby providing for a stable, homogeneous composition of superior anti-calculus control.

The non-ionic organic surface active compounds which are contemplated are commercially known and comprise water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, mercaptans, sulphonamides, etc. The ethylene oxide condensates with higher-alkyl phenols represent a preferred class of non-ionic compounds. Usually the hydrophobic moiety should contain at least about 6 carbon atoms, and preferably at least about 8 carbon atoms, and may contain as many as about 50 carbon atoms or more. The amount of alkylene oxide will vary considerably, depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like, may also be used or substituted in part for the ethylene oxide. Other non-ionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other non-ionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of non-ionic products are the oxyalkylated higher aliphatic alcohols. The fatty alcohols should contain at least 6 carbon atoms, and preferably at least about 8 carbon atoms. The most preferred alcohols are lauryl, myristyl, cetyl, stearyl and oleyl alcohols and the acid alcohols should be condensed with at least about 6 moles of ethylene oxide, and preferably about 10 to 30 moles of ethylene oxide. A typical non-ionic product is oleyl alcohol condensed with 15 moles of ethylene oxide. The corresponding alkyl mercaptans when condensed with ethylene oxide are also suitable in the compositions of the present invention.

The amount of non-ionic may generally be varied from about 0.2–3.0% by weight of the total formulation, depending on the specific nature of the non-ionic utilized, as well as on the amounts and nature of the other ingredients in the oral formulation.

Although this invention has been described with reference to specific examples, it will be apparent to one skilled in the art that various modifications may be made thereto which fall within its scope.

What is claimed is:

1. An oral composition comprising a dental cream, mouthrinse, troche or lozenge, chewing gum, dental tablet or powder or mouthspray containing as the essential anticalculus agent, a magnesium polycarboxylate complex of a magnesium compound and a polycarboxylate compound in the ratio of 1:40 to about 4:1 magnesium compound to polycarboxylate and having a pH of about 4.5–7.8, wherein said polycarboxylate contains ionizable carboxyl groups and is tricarboxy-oxa-butanol or pentanol and is ionically bound to a dissociable, physiologically acceptable magnesium compound, wherein said magnesium compound constitutes about 0.01–5% by weight and the polycarboxylate constitutes about 0.1–10% by weight of the compound.

2. A composition in accordance with claim 1, wherein the tricarboxy compound is the trisodium salt of 3-oxa-2,2,4 tricarboxybutanol-1.

3. A composition in accordance with claim 1, wherein said magnesium compound is magnesium oxide.

4. A composition in accordance with claim 1, wherein said magnesium compound is magnesium chloride.

5. A method of preventing and controlling dental calculus which comprises applying the composition of claim 1 to the oral cavity, wherein the magnesium polycarboxylate complex adsorbs onto the oral surfaces forming a reservoir of magnesium ions which is slowly released within said cavity.

6. A method in accordance with claim 5 which comprises washing the oral cavity with an aqueous mouthrinse.

7. A method in accordance with claim 5 which comprises brushing the teeth with a dental cream.

* * * * *